(12) United States Patent
Liao et al.

(10) Patent No.: US 8,603,092 B2
(45) Date of Patent: Dec. 10, 2013

(54) BONE REPAIRING KIT AND METHOD FOR BONE REPAIR

(75) Inventors: Chun-Jen Liao, Taipei (TW);
Ching-Chuan Jiang, Taipei (TW);
Sung-Ching Chen, Xindian (TW);
Pei-Chi Hsu, Taipei (TW); Shih-Jui Han, Houli Township, Taichung County (TW)

(73) Assignee: Industrial Technology Research Institute, Hsinchu (TW)

( * ) Notice: Subject to any disclaimer, the term of this patent is extended or adjusted under 35 U.S.C. 154(b) by 384 days.

(21) Appl. No.: 12/830,536

(22) Filed: Jul. 6, 2010

(65) Prior Publication Data

US 2011/0160732 A1 Jun. 30, 2011

(30) Foreign Application Priority Data

Dec. 29, 2009 (TW) .............................. 98145620 A

(51) Int. Cl.
*A61B 17/16* (2006.01)
*A61B 17/56* (2006.01)

(52) U.S. Cl.
USPC ................... 606/80; 606/89; 606/95; 606/65; 606/96; 623/23.11; 623/23.12; 623/23.15

(58) Field of Classification Search
USPC .................. 606/79–85, 86 R, 87–91, 95–100; 623/23.48; 144/46, 74, 104, 221, 241; 30/103–108
See application file for complete search history.

(56) References Cited

U.S. PATENT DOCUMENTS

| | | | | |
|---|---|---|---|---|
| 89,624 | A * | 5/1869 | Boyle | 30/494 |
| 1,123,472 | A * | 1/1915 | Bohlig | 30/494 |
| 1,185,762 | A * | 6/1916 | Bohlig | 30/494 |
| 1,279,734 | A * | 9/1918 | McArthy | 30/494 |
| 5,351,587 | A * | 10/1994 | Griffin | 82/113 |
| 5,885,293 | A * | 3/1999 | McDevitt | 606/80 |
| 6,045,580 | A * | 4/2000 | Scarborough et al. | 623/17.11 |
| 6,306,142 | B1 * | 10/2001 | Johanson et al. | 606/79 |
| 6,315,795 | B1 * | 11/2001 | Scarborough et al. | 623/17.11 |

(Continued)

FOREIGN PATENT DOCUMENTS

CN 1709206 A 12/2005

OTHER PUBLICATIONS

English language translation of abstract of CN 1709206A (Published Dec. 21, 2005).

*Primary Examiner* — Todd Manahan
*Assistant Examiner* — Marcela I Shirsat
(74) *Attorney, Agent, or Firm* — McClure, Qualey & Rodack, LLP

(57) ABSTRACT

A bone repairing kit including a drilling device, a pushing device, a clamping member and a hole saw is provided. An end of a tube body of the drilling device is a knife portion. When the tube body rotates with respect to a femur, a bone column is cut by the knife portion and located in the tube body. The pushing device includes a hollow tube and a push bar. The hollow tube is for receiving the tube body. The push bar is for touching and pushing the bone column in the tube body. The clamping member is for clamping the bone column. The hole saw includes a receiving body and cutting knives. The receiving body has a recess for receiving an end of the bone column. The cutting knives surrounding on an inner wall of the recess are for cutting an edge of the end of the bone column.

28 Claims, 8 Drawing Sheets

(56) References Cited

U.S. PATENT DOCUMENTS

| | | | |
|---|---|---|---|
| 6,412,376 B1 * | 7/2002 | Borgia, Jr. | 82/113 |
| 6,607,561 B2 * | 8/2003 | Brannon | 623/23.11 |
| 6,827,720 B2 | 12/2004 | Leali | |
| 7,226,481 B2 | 6/2007 | Kuslich | |
| 2003/0135214 A1 | 7/2003 | Fetto et al. | |
| 2004/0138748 A1 * | 7/2004 | Boyer et al. | 623/16.11 |
| 2006/0149362 A1 | 7/2006 | Pedrozo et al. | |
| 2009/0070980 A1 * | 3/2009 | Livesay | 29/426.5 |

* cited by examiner

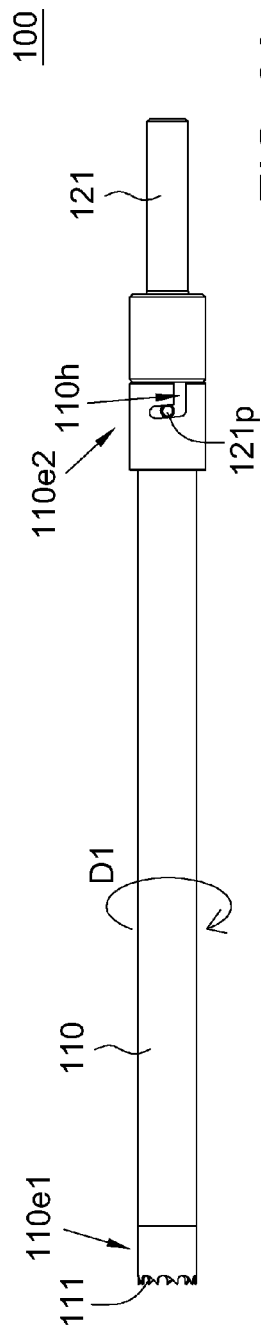
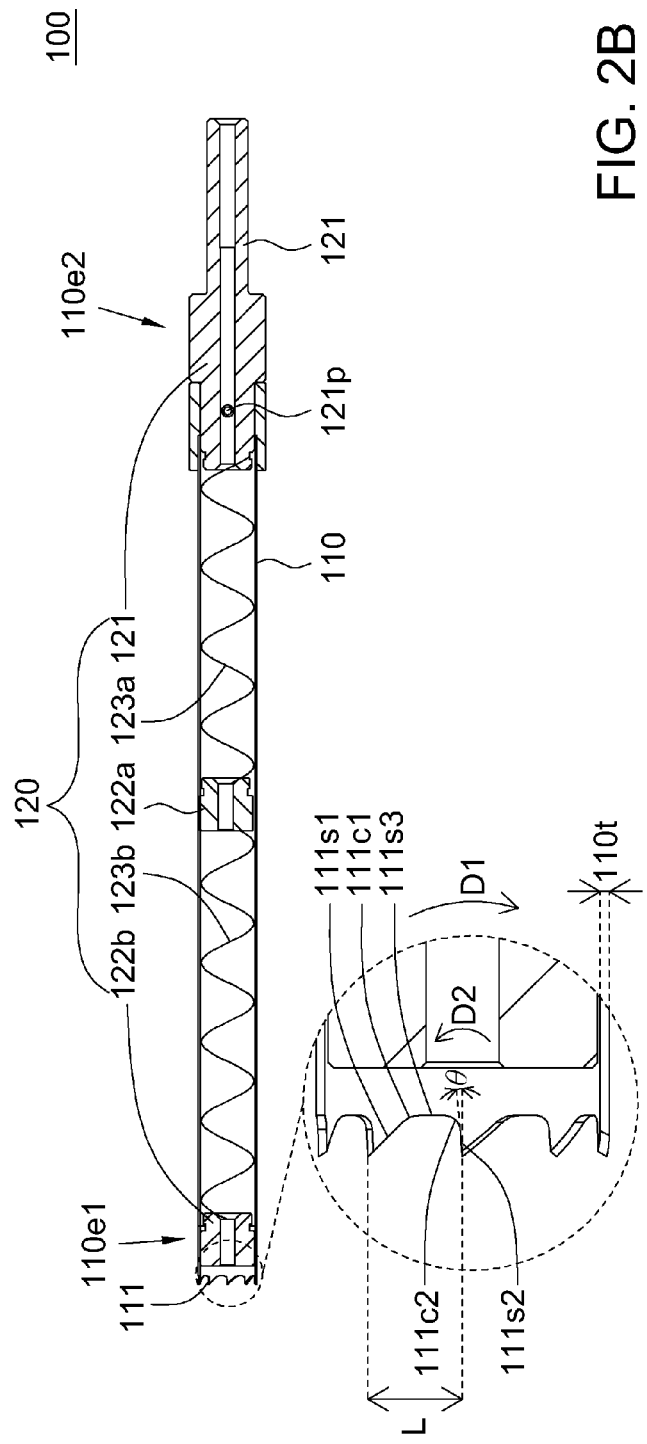

BONE REPAIRING KIT AND METHOD FOR BONE REPAIR

This application claims the benefit of Taiwan application Serial No. 098145620, filed Dec. 29, 2009, the subject matter of which is incorporated herein by reference.

TECHNICAL FIELD

The disclosure relates in general to a bone repairing kit and a method for bone repair, and more particularly to a bone repairing kit which is capable of rebuilding a femur with osteonecrosis and a method for bone repair.

BACKGROUND

There are sixty bones in the lower extremity of the human body, and two of the bones are femurs. The femur is the longest and strongest bone in the lower extremity of the human body. The femur has a hemispherical joint surface, and the femur is embedded into the acetabulum to form the hip joint. As the femur has to support the weight from the body, once pathological changes are found in the hip joint, the patient is unable to move normally, so that the patient's life quality is seriously affected.

Generally speaking, when the blood deliver and supply of the human body show the abnormality, it may cause necrosis of the tissues or organs. In terms of bones, when the deliver of blood is blocked to affect the transfer of oxygen, nutrition and metabolite, osteonecrosis occurs easily. According to the clinical experience, osteonecrosis occurs in the femur frequently. In the early stages of osteonecrosis of the femur, the core decompression is a commonly used treatment. For the first and the second stages of osteonecrosis, the core decompression is effective to 70% of the patients. However, for the third stage of osteonecrosis, the success rate of the core decompression is only 20%.

In addition, as shown in many research results, although the core decompression can ease the pain from osteonecrosis of the femur, the core decompression can not prevent the illness from deteriorating. As a result, the patient can only accept the replacement of the femur or the hip joint in the later stages (the fourth to the sixth stage) of osteonecrosis, that is, when the femur collapses and arthritis occurs in the femur. Therefore, the patient's life quality is affected, and the medical treatment cost is increased.

SUMMARY

The disclosure is directed to a bone repairing kit and a method for bone repair. An osteonecrosis area in the femur of a patient can be rebuilt and repaired. Therefore, the patient's femur can be rebuilt and repaired in a single stage surgery without leaving the operating table, so that the repair effect is good through the short time operation.

According to one embodiment of the invention, a bone repairing kit including a drilling device, a pushing device, a clamping member and a hole saw is provided. The drilling device includes a tube body. An end of the tube body is a knife portion. The tube body is rotated with respect to a femur, so that a bone column is cut from the femur by the rotated knife portion. The bone column is located in the tube body. The pushing device includes a hollow tube and a push bar. The hollow tube is used for receiving the tube body. The push bar is used for touching and pushing the bone column in the tube body from an end of the hollow tube when being rotated with respect to the hollow tube, so that the bone column is pushed out from the tube body. The clamping member is used for clamping the pushed bone column. The hole saw includes a receiving body and several cutting knives. The receiving body has a recess for receiving an end of the bone column. The cutting knives surround on an inner wall of the recess and used for cutting an edge of the end of the bone column when being rotated with respect to the bone column.

According to another embodiment of the invention, a drilling device including a tube body and a guiding assembly is provided. An end of the tube body is a knife portion. The guiding assembly includes a positioning hollow shaft, a first positioning ring and a first elastic member. The positioning hollow shaft is detachably coupled to the other end of the tube body, and used for being connected to a rotating mechanism so as to drive the tube body to rotate when receiving a rotating power. The first positioning ring is used for being received in the tube body. The first elastic member is connected between the positioning hollow shaft and the first positioning ring.

According to still another embodiment of the invention, a pushing device used for pushing an object from a receiver is provided. The pushing device includes a hollow tube and a push bar. The hollow tube is used for receiving the receiver. The push bar has a body and a touching member. The body is rotatably coupled to the hollow tube, and an end of the body is rotatably received in the touching member. When the body rotates with respect to the hollow tube, the touching member non-rotatably touches and pushes the object in the receiver from an end of the hollow tube.

According to yet another embodiment of the invention, a clamping member used for fixing an object is provided. The clamping member includes a clamping body, several elastic fixing clamps and a cover. The clamping body has a fillister which is used for receiving the object. The elastic fixing clamps extend outward from the clamping body so as to surround the object. The cover is put around the elastic fixing clamps, so that the elastic fixing clamps are pushed inward to fix the object.

According to yet another embodiment of the invention, a hole saw used for cutting an object is provided. The hole saw includes a receiving body and several cutting knives. The receiving body has a recess for receiving an end of the object. The cutting knives surrounds on an inner wall of the recess and used for cutting an edge of the end of the object when being rotated with respect to the object.

According to yet another embodiment of the invention, a method for bone repair is provided. A bone column is obtained from a femur, wherein the bone column has an osteonecrosis area. After that, the osteonecrosis area is removed from the bone column. Then, an end of the bone column is shaped. After that, the end of the bone column is put into a cavity of a carrier. Then, the bone column is replaced into the femur.

The invention will become apparent from the following detailed description of the preferred but non-limiting embodiments. The following description is made with reference to the accompanying drawings.

BRIEF DESCRIPTION OF THE DRAWINGS

FIGS. 2A and 2B are an assembling figure and an exploded figure of the drilling device according to a preferred embodiment of the present invention, respectively.

DETAILED DESCRIPTION

The steps of repairing a femur by using a bone repairing kit according to the one embodiment of the invention are firstly illustrated by FIGS. 1A~1F. Referring to FIGS. 1A~1F, the steps of repairing a femur by using a bone repairing kit are shown. The bone repairing kit including a drilling device 100, a pushing device 200, a clamping member 300 and a hole saw 400 is used for repairing the femur of a patient.

Figure 1A:
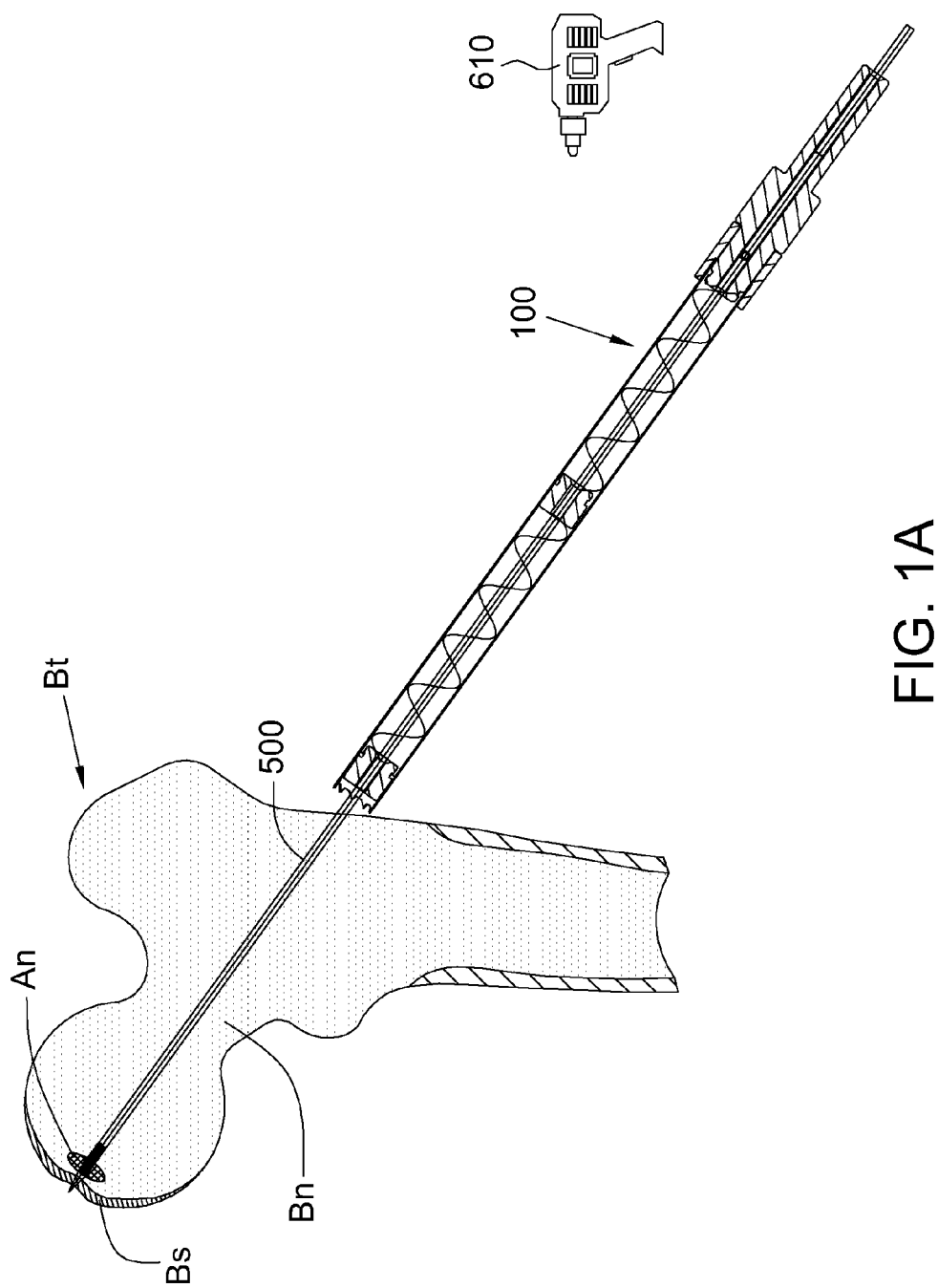
FIGS. 1A~1F are the steps of repairing a femur by using a bone repairing kit.

As shown in FIG. 1A, let the femur Bt of the patient have an osteonecrosis area An as an example. The femur Bt is repaired in the one embodiment of the invention. In order to position the osteonecrosis area An and the location and direction for drilling, a guide pin 500 is, for example, drilled into the femur Bt and passes through the femoral neck Bn, the center of the osteonecrosis area An and the cartilage Bs of the joint.

Figure 1B:
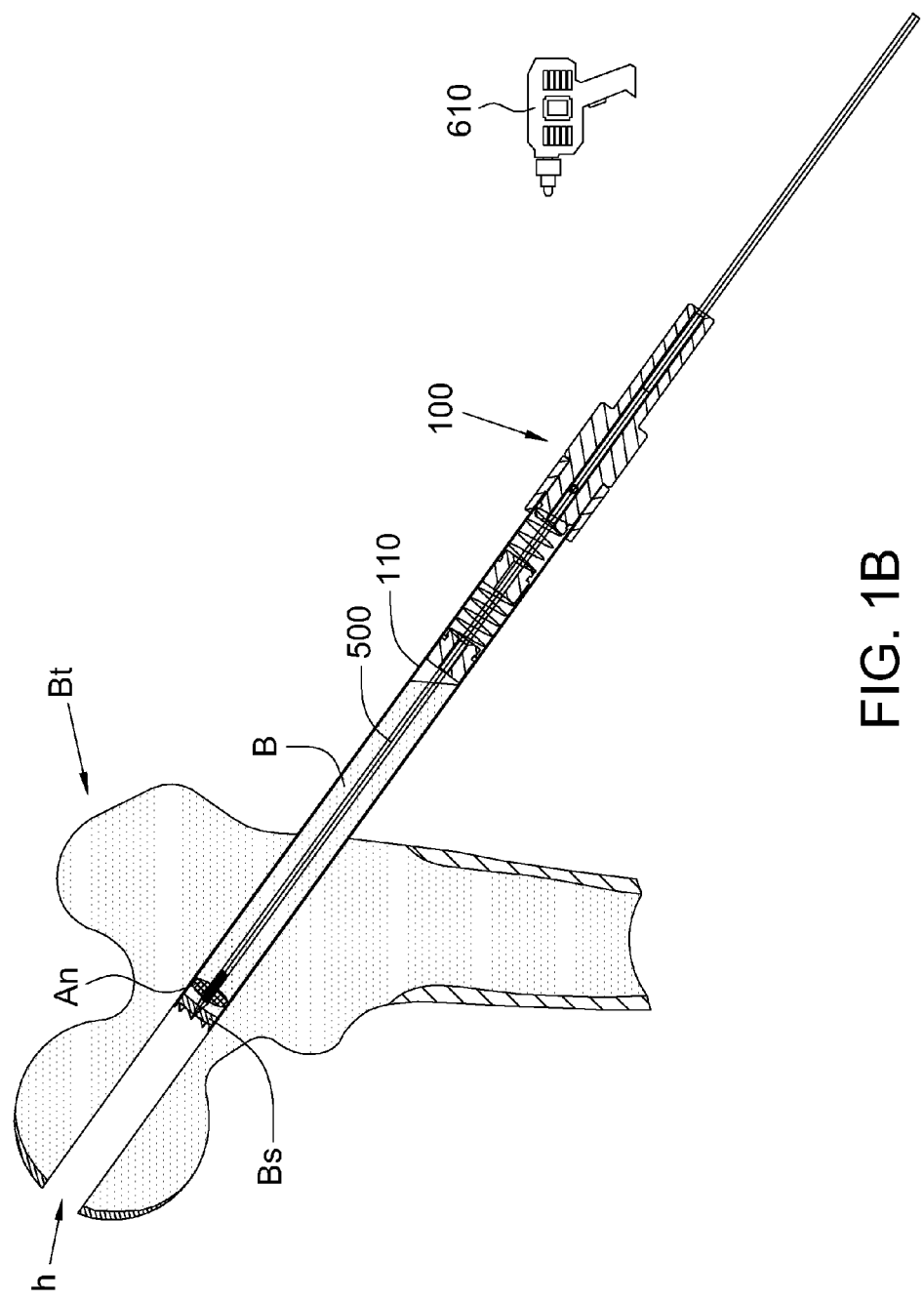

The rotating mechanism 610 is connected to the drilling device 100 so as to drive the drilling device 100 to rotate with respect to the femur Bt. The bone column B is obtained by cutting as the drilling device 100 moves along the guide pin 500, as shown in FIG. 1B. The obtained bone column B is located in the tube body 110 of the drilling device 100, and includes the hard bone, the cartilage Bs and the osteonecrosis area An. A tunnel h is formed in the femur Bt.

Figure 1C:
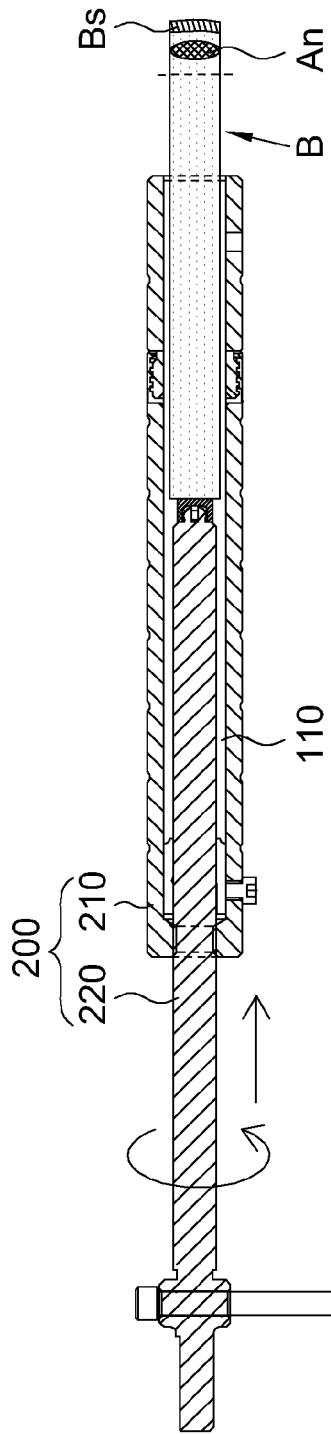

As shown in FIG. 1C, in order to take out the bone column B in the tube body 110, the hollow tube 210 of the pushing device 200 receives the tube body 110 therein, and the push bar 220 of the pushing device 200 pushes the bone column B from an end of the tube body 110. The osteonecrosis area An and the cartilage Bs of the pushed bone column B is, for example, cut off along the dotted line in FIG. 1C.

Figure 1D:
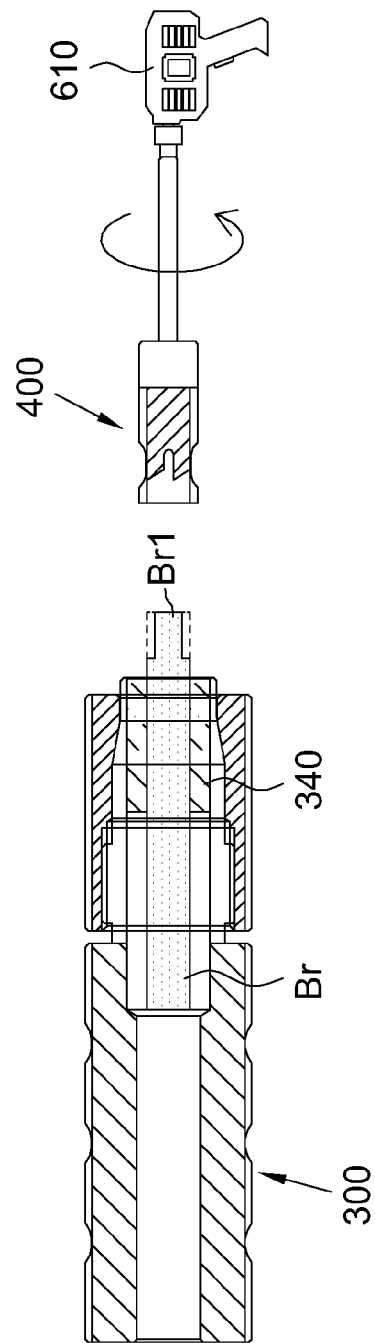

As shown in FIG. 1D, the bone column Br without the osteonecrosis area An and the cartilage Bs is clamped by the clamping member 300, and the hole saw 400 connected to the rotating mechanism 610 is rotated with respect to the bone column Br so as to shape an end of the bone column Br. As shown in FIG. 1D, the bone column Br has a protruding portion Br1. The radius of the protruding portion Br1 is smaller than those of the other parts of the bone column Br.

Figures 1E, 1F:
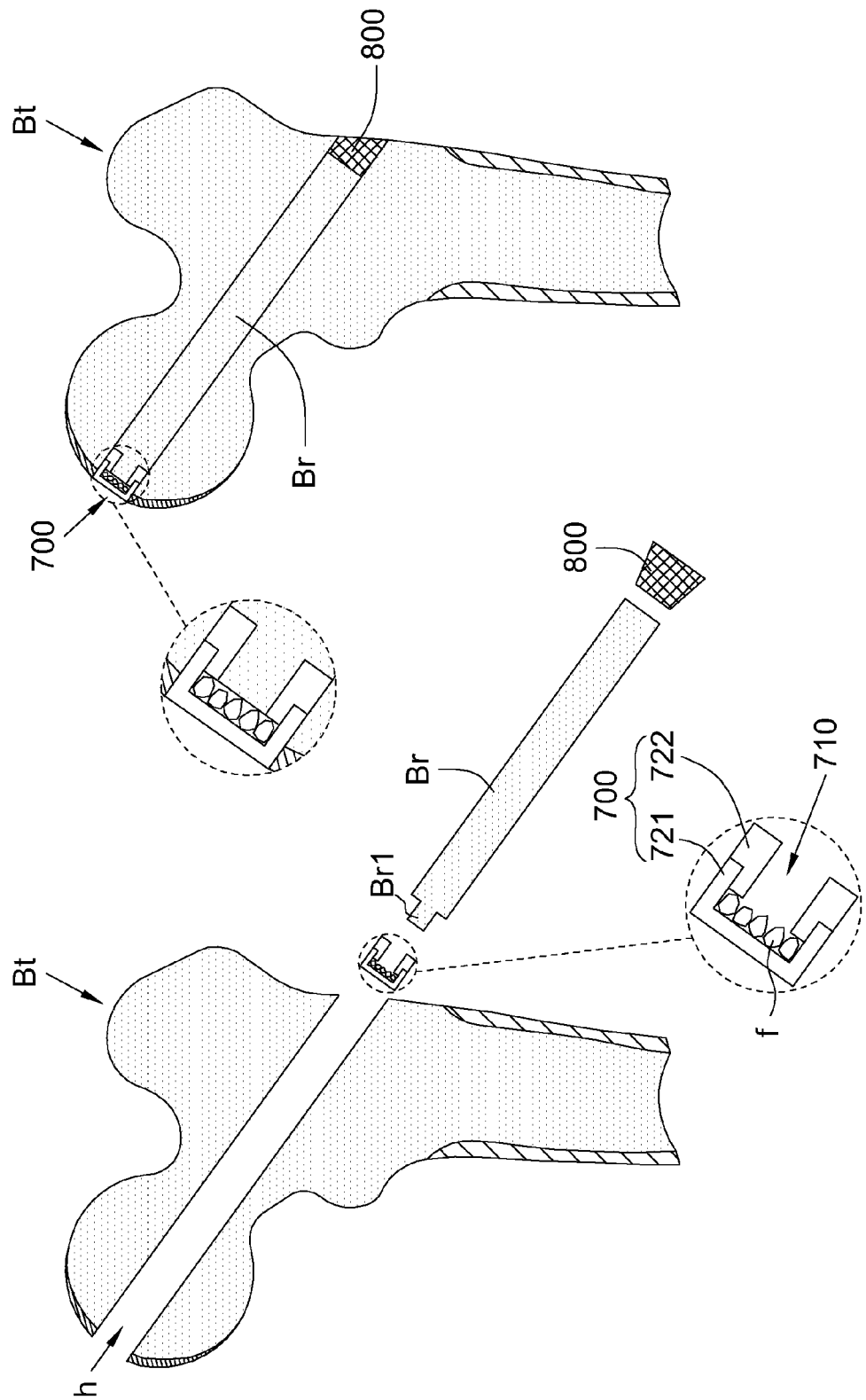

As shown in FIG. 1E, the shaped bone column Br is further processed so as to relocate into the tunnel h of the femur Bt.

As shown in FIG. 1F, the fixing member 800 is disposed at the terminal end of the bone column Br so as to fix the bone column Br in the femur Bt. Therefore, the treatment and repair of the femur Bt are achieved.

The steps of the method for bone repair and the structure and operation of each of the components of the bone repairing kit are elaborated as follows.

The drilling device 100 shown in FIGS. 1A and 1B is firstly described. Referring to FIGS. 2A and 2B, an assembling figure and an exploded figure of the drilling device 100 according to an embodiment of the invention are shown. The drilling device 100 is made of stainless steel or titanium alloys, for example, and the drilling device 100 includes the tube body 110 and the guiding assembly 120. The inner radius and the length of the tube body 110 can be determined according to the desired diameter and length of the bone column B. For example, the inner radius of the tube body 110 can range 2~30 mm, and the length of the tube body 110 can range 10~250 mm.

An end 110e1 of the tube body 110 is the knife portion 111. The knife portion 111 has several knives. The knives are arranged to form a cylindrical surface. Therefore, the surface of the bone column B cut by the knives can be smooth, and the inner surface of the tunnel h of the femur Bt and the outer surface of the bone column B can also be smooth. In the embodiment of the invention, the profile of each of the knives has a first slanting side 111s1, a second slanting side 111s2 and a bottom side 111s3 so as to form a concave. The first slanting side 111s1, the bottom side 111s3 and the second slanting side 111s2 are connected sequentially in the rotating direction D1 of the tube body 110. The second slanting side 111s2 slants towards the direction D2 which is opposite to the rotating direction of the tube body by an angle θ, and the angle θ ranges 1°~8°. For example, if the tube body 110 rotates clockwise in the direction D1 and the clockwise direction D1 is positive, the angle θ that second slanting side 111s2 slants towards can be, for example, −1°~8°. Therefore, when the fiber cortical bone is cut by the knives, the situation that the surface of the bone is torn can be reduced. In addition, in order to reduce the fiction generated when the chips are removed and avoid the heat generated when the cutting process is performed to damage the tissue, the profile of each of the knives further has curved surfaces 111c1 and 111c2. The curved surface 111c1 is located between the first slanting side 111s1 and the bottom side 111s3, and the curved surface 111c2 is located between the bottom side 111s3 and the second slanting side 111s2. If a length formed by projecting the first slanting side 111s1, the bottom side 111s3 and the second slanting side 111s2 onto a surface is a blade portion length L, the radius of curvature of the curved surface 111c1 is 0.1~0.3 times the blade portion length L, and the radius of curvature of the curved surface 111c2 is 0.2~0.5 times the blade portion length L.

In addition, the wall thickness 110t of the tube body 110 is an important factor to affect the magnitude of the axial resistance when the cutting process is performed and the bone regeneration after the bone column is relocated in the tunnel h. When the wall thickness 110t of the tube body 110 is too thick, the gap between the bone column relocated in the tunnel h and the inner surface of the tunnel h is too large, so that the gap may be filled by the fiber tissue firstly to affect the bone regeneration. Therefore, the wall thickness 110t of the tube body 110 according to the present embodiment of the invention ranges 0.1~2 mm, for example, so that the axial resistance generated when the cutting process is performed can be reduced and the bone regeneration is not affected. Preferably, the wall thickness 110t of the tube body 110 is 0.25 mm.

The guiding assembly 120 includes the positioning hollow shaft 121, the first positioning ring 122a, the second positioning ring 122b, the first elastic member 123a and the second elastic member 123b. The positioning hollow shaft 121 detachably coupled to the other end 110e2 of the tube body 110 is used for being connected to the rotating mechanism 610. The first positioning ring 122a and the second positioning ring 122b are received in the tube body 110. The first elastic member 123a is connected between the positioning hollow shaft 121 and the first positioning ring 122a, and the second elastic member 123b is connected between the first positioning ring 122a and second positioning ring 122b.

In the one embodiment of the invention, the connection between the positioning hollow shaft 121 and the tube body 110 is achieved by inserting the pin 121p of the positioning hollow shaft 121 into the sliding groove 110h of the end 110e2 of the tube body 110. A portion of the sliding groove 110h extends from the end 110e2 of the tube body 110 towards the end 110e1 of the tube body 110, and the other portion of the sliding groove 110h extends towards a direction which is opposite to the rotating direction of the tube body 110. Therefore, when the positioning hollow shaft 121 is driven to rotate by the rotating mechanism 610, the pin 121p leans against the inner wall of the sliding groove 110h according to the shape design of the sliding groove 110h, so that the positioning hollow shaft 121 can be stably coupled to the tube body 110.

As shown in FIGS. 1A, 1B, 2A and 2B, when the positioning hollow shaft 121 is connected to the rotating mechanism 610 such as an electrical drill, and the rotating power is outputted to the positioning hollow shaft 121 by the rotating mechanism 610, the positioning hollow shaft 121 coupled to the tube body 110 receives the rotating power so as to drive the tube body 110 to rotate with respect to the femur Bt. As the guide pin 500 passes through the positioning hollow shaft 121, the first elastic member 123a, the first positioning ring 122a, the second elastic member 123b and the second positioning ring 122b sequentially, the tube body 110 moves along the guide pin 500. Therefore, the bone column B which is cut by the knives of the knife portion 111 is gradually received into the tube body 110 and pushes the second positioning ring 122b. As the cut bone column B becomes longer, the second positioning ring 122b moves towards the first positioning ring 122a more, and the first elastic member 123a and the second elastic member 123b are compressed. Lastly, the bone column B being a porous structure is located in the tube body 110 because of the pressure, and the guiding assembly 120 can be separated from the tube body 110 according to the detachability feature. Therefore, the tunnel h is formed in the femur Bt.

Figure 3A:
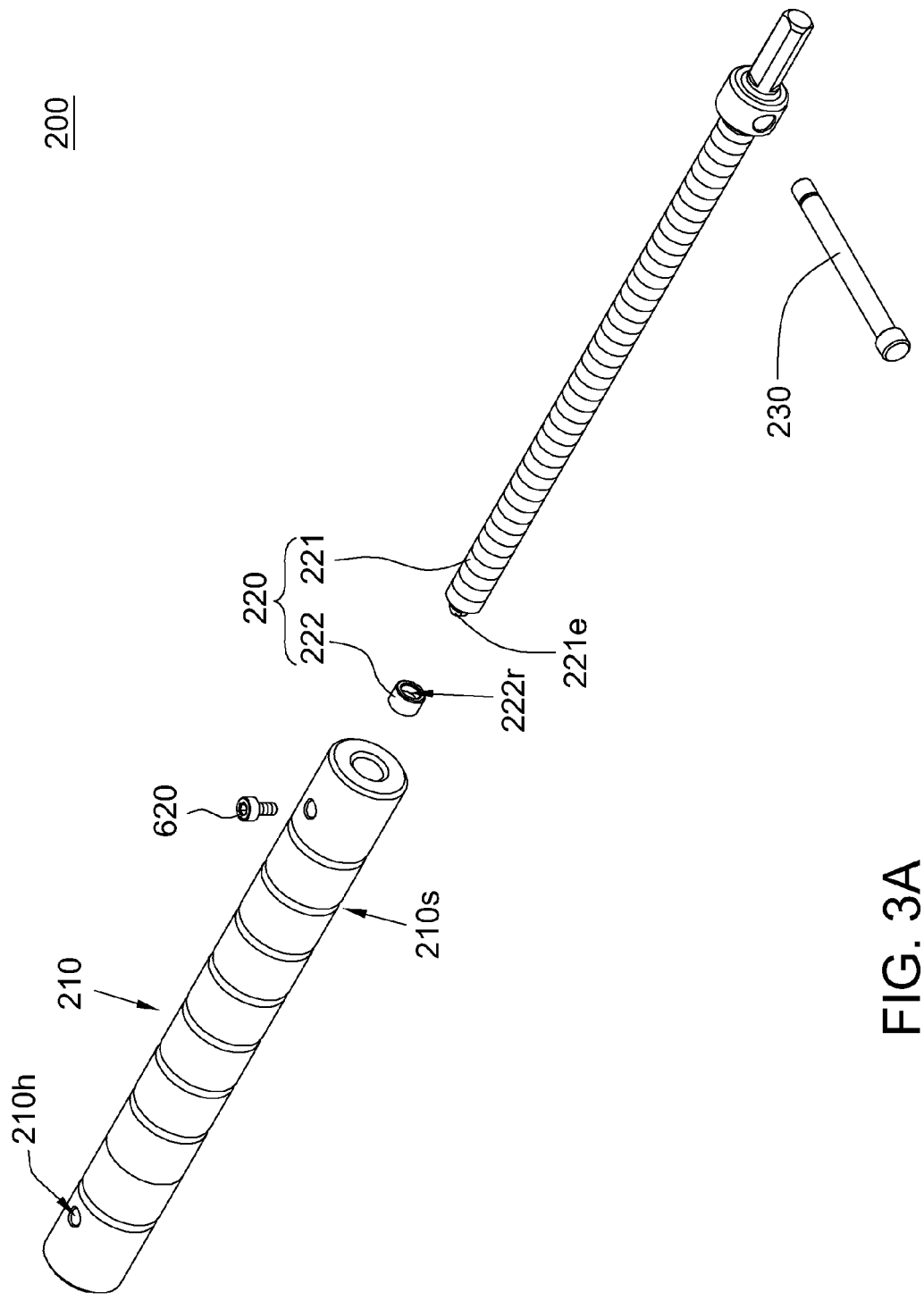
FIGS. 3A and 3B are an exploded figure and a sectional view of the pushing device, respectively.
Figure 3B:
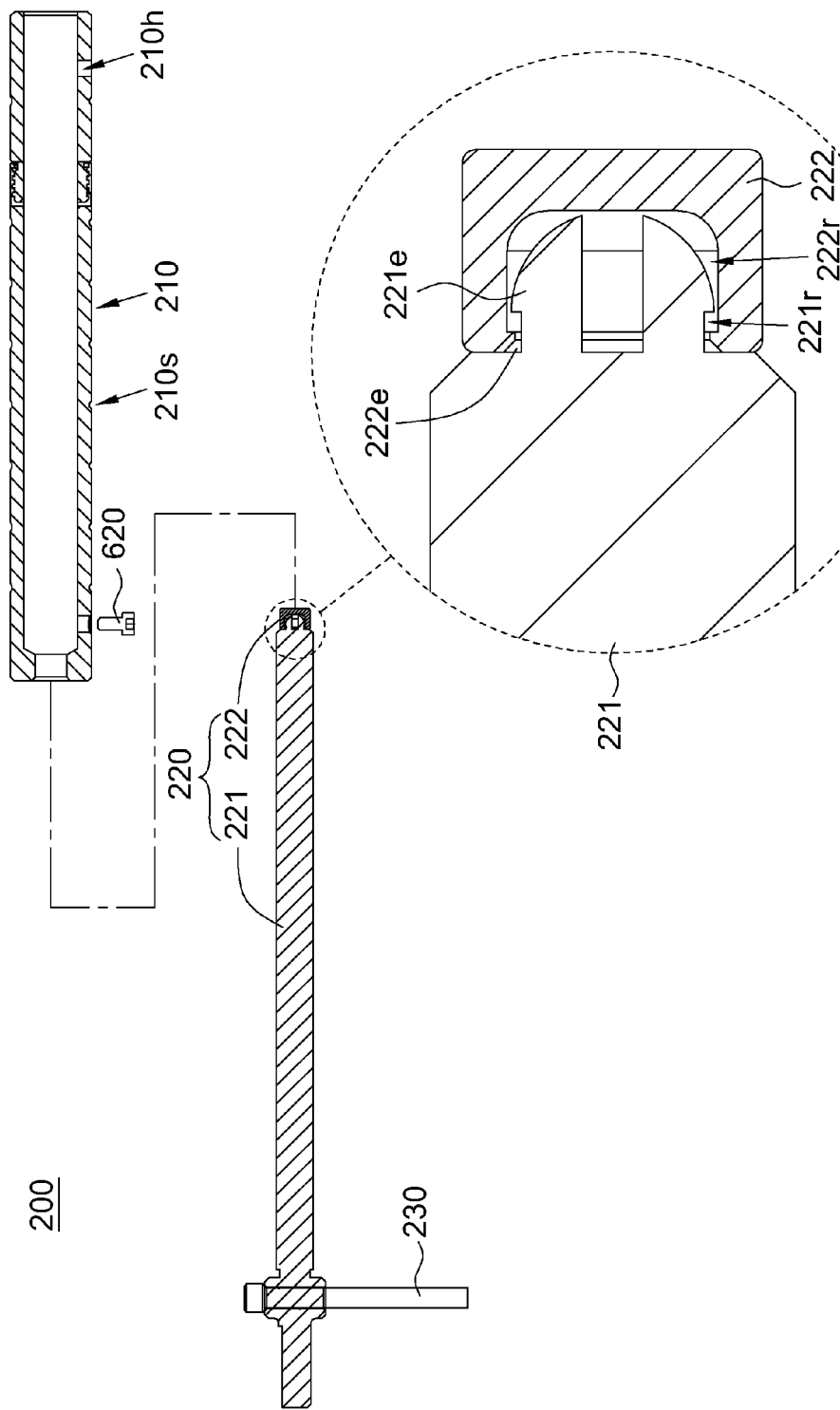

Then, the pushing device 200 in FIG. 1C is elaborated herein. In order to take out the bone column B in the tube body 110, the pushing device 200 in FIGS. 3A and 3B is used for pushing the bone column B in the present embodiment of the invention. Referring to FIGS. 3A and 3B, an exploded figure and a sectional view of the pushing device 200 are shown, respectively. The pushing device 200 includes the hollow tube 210 and the push bar 220. The hollow tube 210 is used for receiving the tube body 110 with the bone column B therein. The push bar 220 is used for touching and pushing the bone column B in the tube body 110 from an end of the hollow tube 210 when being rotated with respect to the hollow tube 210, so that the bone column B is pushed out from tube body 110.

In the one embodiment of the invention, the tube body 110 is fixed in the hollow tube 210 by the screw 620, for example. The push bar 220 has the body 221 and the touching member 222. The body 221 is rotatably coupled to the hollow tube 210 by way of being bolted to the hollow tube 210, and is connected to the handle 230. An end 221e of the body 221 which is, for example, in shape of a sphere is rotatably received in the spherical recess 222r of the touching member 222. The end 221e of the body 221 has a ring recess 221r, and the touching member 222 has the engaging portion 222e. The engaging portion 222e is engaged in the ring recess 221r, so that the end 221e of the body 221 is received in the spherical recess 222r.

In addition, the hollow tube 210 has a hole 210h and several anti-slide grooves 210s. The hole 210h is used for confirming if the tube body 110 is put into the hollow tube 210. The anti-slide grooves 210s located at the outer surface of the hollow tube 210 are used for increasing the fiction when the medical personnel holds the hollow tube 210, so that the situation that the hollow tube 210 is slipped off from the hand of the medical personnel can be avoided.

Therefore, as shown in FIGS. 1C, 3A and 3B, the medical personnel can use one hand to hold the hollow tube 210, and use the other hand to drive the body 221 to rotate with respect to the hollow tube 210 through the handle 230. The spherical end 221e of the body 221 is rotatably received in the spherical recess 222r of the touching member 222. Therefore, when the body 221 is rotated with respect to the hollow tube 210, the touching member 222 is non-rotatably touches the and pushes the bone column B in tube body 110, so that the bone column B is pushed out, and the situation that the bone column B is damaged due to the fiction can be avoided. The bone column B pushed out from the tube body 110 includes the hard bone, the cartilage Bs and the osteonecrosis area An. The cartilage Bs and the osteonecrosis area An of the bone column are cut off along the dotted line.

In the one embodiment of the invention, the hard bone of the bone column B is touched and pushed by the touching member 222, so that the bone column B is pushed out from the tube body 110. However, a person having ordinary skills in the art should know that through the dimension design of the pushing device, the bone column B can be pushed out from the tube body 110 by touching and pushing the cartilage Bs of the bone column B through the touching member 222.

Figure 4A:
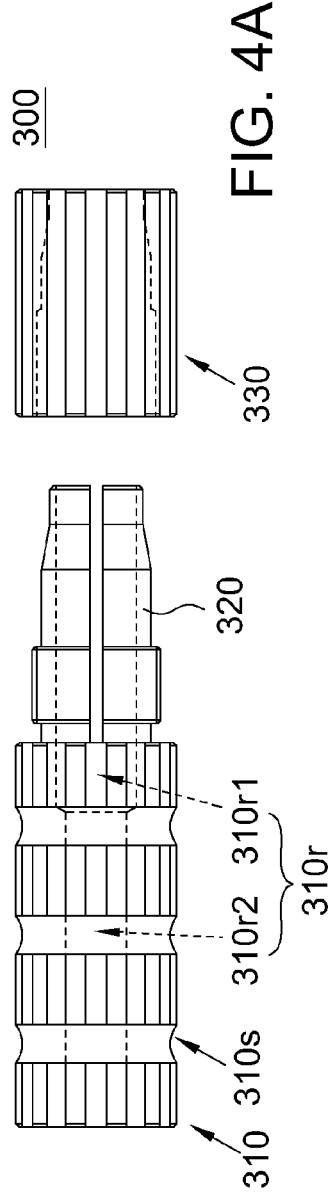
FIGS. 4A and 4B are a side view and an assembly figure of the clamping member according to a preferred embodiment of the present invention, respectively.
Figure 4B:
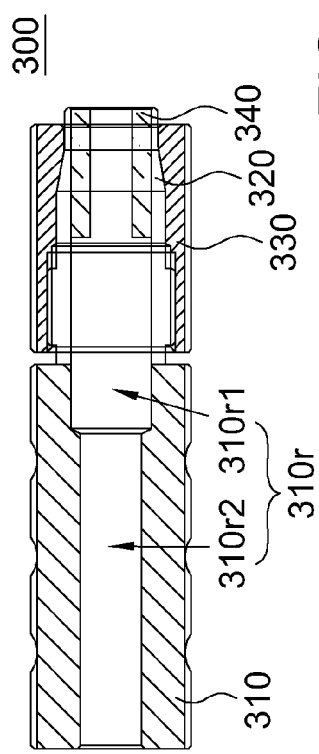

After that, the clamping member 300 and the hole saw 400 in FIG. 1D is further elaborated. The clamping member 300 clamps the remained bone column Br, and the hole saw 400 shapes the bone column Br. Referring to FIGS. 4A and 4B, a side view and an assembly figure of the clamping member 300 according to an embodiment of the invention are shown, respectively. The clamping member 300 includes the clamping body 310, several elastic fixing clamps 320 and the cover 330. The clamping body 310 has the fillister 310r used for receiving the bone column Br. The elastic fixing clamps 320 extend outward from the clamping body 310 so as to surround the bone column Br. The cover 330 is put around the elastic fixing clamps 320, so that the elastic fixing clamps 320 are pushed inward to fix the bone column Br.

The outer surface of the clamping body 310 has several anti-slide grooves 310s. The anti-slide grooves 310s are used for increasing the fiction when the medical personnel holds the clamping body 310, so that the situation that the clamping body 310 is slipped off from the hand of the medical personnel can be avoided. In addition, in order to avoid the bone column Br being damaged due to the clamp of the elastic fixing clamps 320, the clamping member 300 can further includes a protecting ring 340. The protecting ring 340 is put around the bone column Br so as be located between the bone column Br and the elastic fixing clamps 320. Therefore, when the bone column Br is pressed by the elastic fixing clamps 320 as the cover 330 is put around the elastic fixing clamps 320, the protecting ring 340 such as silicon provide a buffer function so as to avoid the bone column Br being damaged. In addition, the fillister 310r has a first groove 310r1 and a second groove 310r2. The first groove 310r1 is connected to the second groove 310r2, and the inner radius of the first groove 310r1 is greater than the inner radius of the second groove 310r2, so that the protecting ring 340 can be positioned between the elastic fixing clamps 320 and the bone column Br through the inner radius difference between the first groove 310r1 and the second groove 310r2.

Figure 5B:
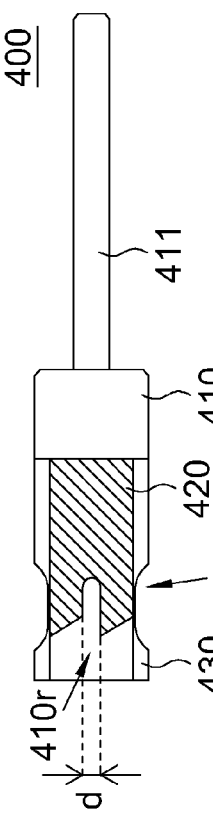
FIGS. 5A and 5B are a front view and a sectional view of the hole saw according to a preferred embodiment of the invention, respectively.
Figure 5A:
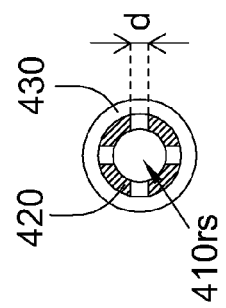

Referring to FIGS. 5A and 5B, a front view and a sectional view of the hole saw 400 according to an embodiment of the invention are shown, respectively. The hole saw 400 includes a receiving body 410 and several cutting knives 420. The receiving body 410 had a recess 410r. The cutting knives 420 surround on an inner wall of the recess 410r, and the bottom surface 410rs of the recess 410r is lower than the cutting knives 420. In the one embodiment of the invention, the two adjacent cutting knives 420 are spaced out a distance d apart, and the receiving body 410 has several holes 410h. The position of the hole 410h corresponds to the distance d so as to facilitate the removal of the chips.

As shown in FIGS. 1D, 4A, 4B, 5A and 5B, when the hole saw 400 starts to cut, the end of the bone column Br clamped by the clamping member 300 is put into the recess 410r through the aligning ring 430 of the hole saw 400. As the aligning ring 430 is fixed at the opening of the recess 410r, the aligning ring 430 guides the bone column Br, so that the bone column Br can be located in the recess 410r precisely. When the spindle 411 of the receiving body 410 is connected to the rotating mechanism 610 such as an electrical drill, the operation of the rotating mechanism 610 is driven the hole saw 400 to rotate with respect to the bone column Br, so that an edge of the end of the bone column Br is cut. As the bottom surface 410rs of the recess 410r is lower than the cutting knives 420, the bottom surface 410rs is used for being a stop surface of the cutting knives 420. That is, when the front surface of the cut end of the bone column Br contacts the bottom surface 410rs of the recess 410r, the cutting knives 420 are unable to cut the bone column Br continuously, so that the cut end of the bone column Br is shaped to have the protruding portion Br1. Therefore, the dimension of the desired bone column Br can be designed according to the dimensions of the cutting knives 420 and the bottom surface 410rs of the recess 410r.

In the one embodiment of the invention, as shown in FIG. 1E, the bone repairing kit can further include the carrier 700 and enzymes. The carrier 700 includes the cartilage portion 721 and the bone portion 722 so as to form the cavity 710. The carrier 700 can be made of a biodegradable material. For example, the cartilage portion 721 can be made of a polymer material, and the bone portion 722 can be made of the combination of a polymer material and a ceramic material so as to provide the strength. The polymer material can be polylactide-glycolic acid (PLGA), and the ceramic material can be tricalcium phosphate (TCP). Or, the carrier 700 can be formed by the patient's decalcified autograft bone. Then, the cartilage Bs cut from the bone column B or the cartilage obtained from the patient's non-weight bearing site is cut into cartilage fragments f, and the dimension of the cartilage fragment f ranges 200~2000 μm, for example. After that, the cartilage fragments f are processed by the enzymes so as to dissolve out portions of cartilage cells. The cartilage fragments f processed by the enzymes are put into the cavity 710 of the carrier 700. Therefore, the protruding portion Br1 of the bone column Br is received into the cavity 710, and the bone column Br is relocated into the tunnel h of the femur Bt.

Preferably, the bone repairing kit can further include the fixing member 800, and the fixing member 800 is in shape of a taper, for example. As shown in 1F, when the bone column Br is relocated into the femur Bt, the fixing member 800 is put at the terminal end of the bone column Br so as to stably fix the bone column Br in the femur Bt. In the present embodiment of the invention, the fixing member 800 can be a flexible biodegradable or non-biodegradable material. Or, the fixing member 800 can be formed by the patient's autograft bone.

The bone repairing kit and the method for bone repair according to the embodiment of the invention, the bone column is obtained from the patient's femur by the drilling device, and the osteonecrosis area is cut off. Then, the bone column located in the tube body is pushed out by the pushing device. After that, the bone column is clamped by the clamping member, so that the edge of the end of the bone column is cut to form the protruding portion by the hole saw. The bone column with the protruding portion is further combined with the carrier so as to replace into the patient's femur. Compared with the treatment of the osteonecrosis area of the femur through the artificial joint replacement, the patient's femur can be rebuilt and repaired in a single stage surgery without leaving the operating table, through the bone repairing kit of the one embodiment of the invention, so that the repair effect is good through the short time operation. Therefore, the patient's life quality can be maintained and the medical treatment cost can be effectively reduced.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A bone repairing kit, comprising:
   a drilling device, comprising:
      a tube body, wherein an end of the tube body is a knife portion, the tube body is rotated with respect to a femur so as to cut a bone column from the femur by the rotated knife portion, and the bone column is located in the tube body;
      a guiding assembly, comprising:
         a first positioning ring used for being received into the tube body;
         a second positioning ring used for being received into the tube body; and
         a elastic member connected between the first positioning ring and the second positioning ring;
   a pushing device, comprising:
      a hollow tube used for receiving the tube body; and
      a push bar used for touching and pushing the bone column in the tube body from an end of the hollow tube when being rotated with respect to the hollow tube, so that the bone column is pushed out from the tube body;
   a clamping member used for clamping the pushed bone column; and
   a hole saw, comprising:
      a receiving body having a recess for receiving an end of the bone column; and
      a plurality of cutting knives surrounding on an inner wall of the recess and used for cutting an edge of the end of the bone column and shaping the end of the bone column to form a protruding portion when being rotated with respect to the bone column.

2. The bone repairing kit according to claim 1, wherein the guiding assembly further comprises:
   a positioning hollow shaft detachably coupled to the other end of the tube body, wherein the positioning hollow shaft is used for being connected to a rotating mechanism so as to drive the tube body to rotate when receiving a rotating power;
   and
   another elastic member connected between the positioning hollow shaft and the first positioning ring.

3. The bone repairing kit according to claim 2, wherein the positioning hollow shaft has a pin, the other end of the tube body has a sliding groove, and the pin is inserted into the sliding groove.

4. The bone repairing kit according to claim 3, wherein a portion of the sliding groove extends from the other end of the tube body towards the end of the tube body, and the other portion of the sliding groove extends towards a direction which is opposite to the rotating direction of the tube body.

5. The bone repairing kit according to claim 1, further comprising:
a guide pin used for passing through the positioning hollow shaft, the another elastic member, the first positioning ring, the elastic member and the second positioning ring, so that the tube body moves along the guide pin.

6. The bone repairing kit according to claim 1, wherein the inner radius and the length of the tube body are determined according to the desired diameter and length of the bone column, the inner radius of the tube body ranges 2~30 mm, and the length of the tube body ranges 10~250 mm.

7. The bone repairing kit according to claim 1, wherein the knife portion has a plurality of knives, the profile of each of the knives has a first slanting side, a second slanting side and a bottom side, and the first slanting side, the bottom side and the second slanting side are connected sequentially in the rotating direction of the tube body.

8. The bone repairing kit according to claim 7, wherein the second slanting side slants towards a direction which is opposite to the rotating direction of the tube body by an angle, and the angle ranges 1°~8°.

9. The bone repairing kit according to claim 7, wherein a length formed by projecting the first slanting side, the bottom side and the second slanting side onto a surface is a blade portion length, the profile of each of the knives further has a curved surface, the curved surface is located between the first slanting side and the bottom side, and the radius of curvature of the curved surface is 0.1~0.3 times the blade portion length.

10. The bone repairing kit according to claim 7, wherein a length formed by projecting the first slanting side, the bottom side and the second slanting side onto a surface is a blade portion length, the profile of each of the knives further has a curved surface, the curved surface is located between the bottom side and the second slanting side, and the radius of curvature of the curved surface is 0.2~0.5 times the blade portion length.

11. The bone repairing kit according to claim 1, wherein the wall thickness of the tube body ranges 0.1~2 mm.

12. The bone repairing kit according to claim 1, wherein the knife portion has a plurality of knives, and the knives are arranged to form a cylindrical surface.

13. The bone repairing kit according to claim 1, wherein the push bar has a body and a touching member, the body is rotatably coupled to the hollow tube, and an end of the body is rotatably received in the touching member;
wherein, when the body rotates with respect to the hollow tube, the touching member non-rotatably touches and pushes the bone column in the tube body.

14. The bone repairing kit according to claim 13, wherein the end of the body of the push bar is in shape of a sphere, and the touching member has a spherical recess for receiving the spherical end of the body.

15. The bone repairing kit according to claim 14, wherein the end of the body of the push bar has a ring recess, the touching member has an engaging portion, and the engaging portion is engaged in the ring recess.

16. The bone repairing kit according to claim 1, wherein the push bar is bolted to the hollow tube.

17. The bone repairing kit according to claim 1, wherein the clamping member comprises:
a clamping body having a fillister which is used for receiving the pushed bone column;
a plurality of elastic fixing clamps extending outward from the clamping body so as to surround the bone column; and
a cover put around the elastic fixing clamps so that the elastic fixing clamps are pushed inward to fix the bone column.

18. The bone repairing kit according to claim 17, wherein the clamping member further comprises:
a protecting ring put around the bone column so as to be located between the bone column and the elastic fixing clamps.

19. The bone repairing kit according to claim 18, wherein the fillister has a first groove and a second groove, the first groove is connected to the second groove, and the inner radius of the first groove is greater than the inner radius of the second groove.

20. The bone repairing kit according to claim 1, wherein two adjacent cutting knives of the cutting knives are spaced out a distance apart.

21. The bone repairing kit according to claim 20, wherein the receiving body has at least one hole, and the position of the hole corresponds to the position of the distance.

22. The bone repairing kit according to claim 1, wherein the recess has a bottom surface and the bone column has a front surface, the bottom surface of the recess is lower than the cutting knives and is used for contacting the front surface of the bone column.

23. The bone repairing kit according to claim 1, wherein the hole saw further comprises:
a aligning ring fixed to an opening of the recess.

24. The bone repairing kit according to claim 1, wherein the receiving body further has a spindle used for being connected to a rotating mechanism.

25. The bone repairing kit according to claim 1, further comprising:
a fixing member used for fixing the bone column into the femur.

26. The bone repairing kit according to claim 25, wherein the fixing member is in shape of a taper.

27. The bone repairing kit according to claim 1, further comprising:
a carrier has a cavity used for receiving the end of the bone column which is cut by the hole saw.

28. The bone repairing kit according to claim 27, wherein the bone repairing kit is used for repairing the femur of a patient, the carrier comprises a cartilage portion and a bone portion so as to form the cavity, and the carrier is made of a biodegradable material or a decalcified autograft bone.

* * * * *